United States Patent [19]
Mattox et al.

[11] Patent Number: 5,910,503
[45] Date of Patent: Jun. 8, 1999

[54] STABLE MICROBICIDE FORMULATION

[75] Inventors: John Robert Mattox, Perkasie; Ethan Scott Simon, Abington; Ramesh Balubhai Petigara, Hatfield, all of Pa.

[73] Assignee: Rohm and Haas Company, Philadelphia, Pa.

[21] Appl. No.: 09/023,939

[22] Filed: Feb. 13, 1998

Related U.S. Application Data

[60] Provisional application No. 60/063,350, Oct. 28, 1997.

[51] Int. Cl.$^6$ ..................................................... A01N 43/80
[52] U.S. Cl. ............................................................ 514/372
[58] Field of Search ............................................. 514/372

[56] References Cited

U.S. PATENT DOCUMENTS

| | | | |
|---|---|---|---|
| 3,870,795 | 3/1975 | Miller et al. | 424/270 |
| 5,137,899 | 8/1992 | Petigara et al. | 514/372 |
| 5,145,501 | 9/1992 | Lashen et al. | 514/372 |
| 5,153,213 | 10/1992 | Schmidt | 514/372 |
| 5,478,797 | 12/1995 | Gironda et al. | 514/372 |
| 5,594,017 | 1/1997 | Mattox | 514/372 |
| 5,668,083 | 9/1997 | Matsumoto | 504/138 |
| 5,703,105 | 12/1997 | Redlich et al. | 514/372 |
| 5,725,806 | 3/1998 | Ghosh | 252/405 |

FOREIGN PATENT DOCUMENTS 5-170608  7/1993  Japan ...................................... 514/372

*Primary Examiner*—James H. Reamer
*Attorney, Agent, or Firm*—S. Matthew Cairns

[57] ABSTRACT

Stable microbicidal compositions containing a 3-isothiazolone compound, metal nitrate, bromic acid, iodic acid, periodic acid, or their salts and water are disclosed. Also disclosed are methods of preventing or reducing precipitate formation in 3-isothiazolone compositions.

11 Claims, No Drawings

STABLE MICROBICIDE FORMULATION

This application claims benefit of Provisional Appln 60/063,350 filed Oct. 28, 1997.

BACKGROUND OF THE INVENTION

This invention relates to the stabilization of microbicides. In particular, this invention relates to the improved stabilization of 3-isothiazolone microbicides.

Microbicides are used commercially to prevent the growth of microbes in a variety of loci, such as cooling towers, metal working fluid systems, paint and cosmetics. One of the more important classes of microbicides is 3-isothiazolones. Many 3-isothiazolones have achieved commercial success because they are very effective in preventing microbial growth under a wide variety of conditions and in a variety of loci. Among the most important 3-isothiazolones are 5-chloro-2-methyl-3-isothiazolone, 2-methyl-3-isothiazolone, and mixtures thereof.

While 3-isothiazolones are very effective microbicides, they suffer from being unstable under certain conditions. Without the presence of a stabilizer, many 3-isothiazolones chemically degrade and lose microbicidal efficacy. Much research has been devoted to stabilizing 3-isothiazolones.

Typical 3-isothiazolone products of a 3:1 mixture of 5-chloro-2-methyl-3-isothiazolone and 2-methyl-3-isothiazolone contain between 1 and 25 percent by weight of the 3-isothiazolone mixture and a similar amount of a stabilizer. Concentrate compositions of a 3:1 mixture of 5-chloro-2-methyl-3-isothiazolone and 2-methyl-3-isothiazolone generally contain about 5 to 35 percent by weight of the 3-isothiazolone compounds and require about 10 to 25 percent by weight of a stabilizer. Dilute solutions of a 3:1 mixture of 5-chloro-2-methyl-3-isothiazolone and 2-methyl-3-isothiazolone contain about 0.5 to 5 percent by weight of the 3-isothiazolone compounds. In general, the compounds that stabilize 3-isothiazolone concentrates do not stabilize 3-isothiazolone dilute solutions. Compounds, such as magnesium nitrate, that do stabilize both 3-isothiazolone concentrates and dilute solutions do so in greatly differing amounts. More magnesium nitrate is required to stabilize a 3-isothiazolone dilute solution than a concentrate, 23 percent by weight for dilute solutions as compared to 12 to 16 percent by weight for concentrates. As dilute solutions are typically prepared by diluting 3-isothiazolone concentrate compositions, this need for additional stabilizer results in increased costs and handling.

Various stabilizers are known for 3-isothiazolones; however, these stabilizers suffer from providing a high metal salt content or providing only limited stability to the 3-isothiazolone. When a 3-isothiazolone stabilized with a metal salt is added to a latex formulation, the high metal salt content can coagulate the latex. JP 05 170 608 A discloses bromic acid, iodic acid, periodic acid or their salts as stabilizers for 3-isothiazolone compositions. This patent application teaches the replacement of bivalent metal salts, such as magnesium nitrate, as stabilizers with bromic acid, iodic acid, periodic acid or their salts. This is not a complete solution to the stability issue, as iodate and periodate salts provide little to no stability for those 3-isothiazolone compositions having a concentration of 10 to 35 percent by weight. This patent application also does not address the problem of precipitate formation upon storage of the 3-isothiazolone compositions.

Although the use of stabilizers, such as metal nitrate salts, enables 3-isothiazolone products to retain their microbicidal efficacy for considerable periods of time, other problems may develop without significant loss of 3-isothiazolones, such as the formation of precipitate upon storage. The presence of this precipitate does not impact the efficacy of the 3-isothiazolones; however, the presence of the precipitate gives undesirable appearance to users of the product. It is clearly preferable from a commercial standpoint to have a product which does not form a precipitate.

Thus, there is a continuing need for stable 3-isothiazolone concentrate compositions that remain stable when diluted to form dilute solutions without the need for additional stabilizer and are free of undesirable precipitate.

SUMMARY OF THE INVENTION

It has now surprisingly been found that a combination of bromic acid, iodic acid, periodic acid, or their salts with a metal nitrate salt, both of which are in amounts that are ineffective in stabilizing 3-isothiazolone concentrates when used alone, is effective in stabilizing 3-isothiazolone concentrates while at the same time avoiding the problems of coagulation of latexes and precipitate formation upon storage.

The present invention is directed to a stable microbicides composition including: (a) 0.5 to 35 wt %, based on the weight of the composition, of a water soluble 3-isothiazolone; (b) 0.2 to 30 wt %, based on the weight of the composition, of a metal nitrate selected from the group consisting of lithium nitrate; sodium nitrate; potassium nitrate; magnesium nitrate; calcium nitrate; and ammonium nitrate; (c) 0.01 to 35 wt %, based on the weight of the composition, of bromic acid, iodic acid, periodic acid, or their salts; and (d) water; wherein the weight ratio of (b) to (a) is 25:1 to 1:25, and the composition is precipitate free.

The present invention is also directed to a method of preventing precipitate formation in a microbicide composition including the step of adding 0.2 to 30 wt %, based on the weight of the composition, of a metal nitrate selected from the group consisting of lithium nitrate; sodium nitrate; potassium nitrate; magnesium nitrate; calcium nitrate; and ammonium nitrate to a stabilized 3-isothiazolone composition comprising 0.5 to 35 wt %, based on the weight of the composition, of a water soluble 3-isothiazolone compound; 0.01 to 35 wt %, based on the weight of the composition, of bromic acid, iodic acid, periodic acid, or their salts; and water; wherein the weight ratio of metal nitrate to 3-isothiazolone compound is 25:1 to 1:25.

The present invention is also directed to a method of controlling or inhibiting the growth of microorganisms in a locus comprising introducing to the locus a composition as described above.

DETAILED DESCRIPTION OF THE INVENTION

As used throughout the specification, the following terms shall have the following meanings, unless the context clearly indicates otherwise.

The term "microbicide" refers to a compound capable of inhibiting the growth of or controlling the growth of microorganisms at a locus. The term "microorganism" includes, but is not limited to, fungi, bacteria, and algae.

As used in this specification, the following abbreviations are applied: HPLC=high performance liquid chromatography; C=centigrade; ppm=parts per million; g=gram; and wt %=percent by weight.

All amounts are percent by weight, unless otherwise noted and all percent by weight ranges are inclusive. All ratios are by weight and all ratio ranges are inclusive.

Any water soluble 3-isothiazolone compound is useful in the compositions of the present invention. Water soluble 3-isothiazolone compounds are those having a water solubility greater than 1000 ppm. Suitable 3-isothiazolone compounds include, but are not limited to: 5-chloro-2-methyl-3-isothiazolone; 2-methyl-3-isothiazolone; 2-ethyl-3-isothiazolone; 5-chloro-2-ethyl-3-isothiazolone; 4,5-dichloro-2-methyl-3-isothiazolone; and mixtures thereof Preferred 3-isothiazolones are 5-chloro-2-methyl-3-isothiazolone and 2-methyl-3-isothiazolone, either alone or in admixture. When mixtures of 5-chloro-2-methyl-3-isothiazolone and 2-methyl-3-isothiazolone are used, the weight ratio of 5-chloro-2-methyl-3-isothiazolone to 2-methyl-3-isothiazolone is generally 99:1 to 1:99, preferably 10:1 to 3:1.

The amount of water soluble 3-isothiazolone compound useful in the compositions of the present invention is 0.5 to 35 wt %, based on the weight of the composition. It is preferred to use 5 to 35 wt %; and more preferably, 5 to 25 wt %.

Bromic acid, iodic acid, periodic acid, or any bromic acid, iodic acid or periodic acid salt which is water soluble and functions to stabilize the 3-isothiazolone compound is useful in the compositions of the present invention. For purposes of the present specification, these compounds will be collectively referred to as "Oxidants." Suitable Oxidants include, but are not limited to: bromic acid; lithium bromate; sodium bromate; potassium bromate; ammonium bromate; iodic acid; lithium iodate; sodium iodate; potassium iodate; ammonium iodate; periodic acid; lithium periodate; sodium periodate; potassium periodate; and ammonium periodate. The Oxidant is preferably iodic acid, periodic acid, or their salts. Lithium iodate; sodium iodate; potassium iodate; ammonium iodate; lithium periodate; sodium periodate; potassium periodate; and ammonium periodate are more preferred. Lithium iodate; sodium iodate; potassium iodate; lithium periodate; sodium periodate; and potassium periodate are especially preferred. Mixtures of Oxidants may be used.

The amount of Oxidant useful in the present invention is 0.01 to 35 wt %, based on the weight of the composition, preferably 0.05 to 10 wt %, and more preferably 1 to 5 wt %. The amount of Oxidant that can be used in the present invention is limited by the solubility of Oxidant in the compositions. For example, when iodic acid or periodic acid is used, it can be used in an amount up to 35 wt % of the composition. The specific amount of iodic acid or periodic acid that can be used depends upon the type and concentration of metal ions present in the composition to be stabilized. In general, the lower the concentration of metal ions, the higher the amount of iodic acid or periodic acid that can be used. When monovalent metal ions are present, generally more iodic acid or periodic acid can be used than when divalent metal ions are present. When an iodate or periodate salt is used, it can be used in an amount up to about 9 wt % of the composition. The specific amount of iodate or periodate salt depends upon the type and concentration of metal ions present in the composition. Typically, the amount of Oxidant necessary to prevent formation of a precipitate is generally sufficient if the weight ratio of Oxidant to 3-isothiazolone compound is 1:1000 to 20:1, preferably 1:800 to 1:1, and most preferably 1:250 to 1:10. Oxidants are generally commercially available, for example, from Aldrich Chemical Company (Milwaukee, Wis.) and are used without further purification.

Any water soluble metal nitrate may be used in the compositions of the present invention. Suitable metal nitrates include, but are not limited to: lithium nitrate, sodium nitrate, potassium nitrate, magnesium nitrate, calcium nitrate, copper nitrate, zinc nitrate, ferric nitrate, and ammonium nitrate. Preferred metal nitrates are lithium nitrate, sodium nitrate, potassium nitrate, magnesium nitrate, calcium nitrate, and ammonium nitrate. Especially preferred are sodium nitrate, potassium nitrate, and magnesium nitrate. More than one metal nitrate may be used advantageously in the compositions of the present invention.

The amount of metal nitrate necessary to stabilize the 3-isothiazolone concentrate compositions of the present invention is typically 0.2 to 30 wt %, based on the weight of the composition. It is preferred to use metal nitrate in an amount between 1 and 25 wt %, and most preferably between 3 and 10 wt %. The amount of metal nitrate is generally sufficient if the weight ratio of metal nitrate to 3-isothiazolone compound is 25:1 to 1:25, and preferably 20:1 to 1:1. The metal nitrates are generally commercially available, for example, from Aldrich Chemical Company (Milwaukee, Wis.) and may be used without further purification.

The weight ratio of metal nitrate to Oxidant is typically 1:150 to 2500:1, preferably 1:50 to 50:1, and most preferably 1:10 to 10:1.

Particularly useful compositions of the present invention comprise 5 to 25 wt % of a water soluble 3-isothiazolone; 1 to 25 wt % of a metal nitrate selected from the group consisting of sodium nitrate; potassium nitrate; and magnesium nitrate; 0.05 to 10 wt % of bromic acid, iodic acid, periodic acid, or their salts; and water. Especially useful compositions are those wherein the bromic acid, iodic acid, periodic acid, or their salts is selected from the group consisting of iodic acid, sodium iodate, potassium iodate, and sodium periodate. All percentages used above are based on the weight of the composition.

In preparing the compositions of the present invention, the Oxidant cannot be added directly to the 3-isothiazolone alone. Otherwise, the 3-isothiazolone, metal nitrate, Oxidant, and water can be mixed in any order. It is preferred that the compositions of the present invention are prepared by adding the Oxidant to a mixture of 3-isothiazolone, metal nitrate, and water.

An advantage of the compositions of the present invention is that they show no visible precipitate formation, even after storage for 8 weeks at 55° C. Even dilute solutions prepared by diluting 3-isothiazolone concentrates of the present invention comprising 3-isothiazolone compounds, metal nitrate, Oxidant, and water, are not only stable against chemical degradation, but are also precipitate free upon storage. In addition, dilute solutions prepared according to the present invention do not need additional stabilizer, thus reducing the cost and extra handling associated with known 3-isothiazolone concentrates. One of the further advantages of the present invention is that the amount of metal salt needed to stabilize 3-isothiazolone concentrates can be reduced, thereby reducing the possibility of coagulation when added to latexes.

The compositions of the present invention can be used to inhibit the growth of microorganisms by introducing a microbicidally effective amount of the compositions onto, into, or at a locus subject to microbial attack. Suitable loci include, but are not limited to: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions;

paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics and toiletries; shampoos; soaps; detergents; industrial disinfectants or sanitizers, such as cold sterilants, hard surface disinfectants; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas. Preferred loci are cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings; and metal working fluids.

The amount of 3-isothiazolone compounds suitable to inhibit or control the growth of microorganisms is well known in the art and depends upon the locus to be protected. The amount of 3-isothiazolone microbicide suitable to inhibit the growth of microorganisms is generally between 0.05 and 5,000 ppm, based on the volume of said locus to be protected. It is preferred to use between 0.1 and 2,500 ppm. For example, loci such as a cooling tower or pulp and paper processing fluids require 0.1 to 100 ppm of the 3-isothiazolone microbicides to inhibit microorganism growth. In cooling towers or pulp and paper processing fluids, it is preferred to use between 0.1 and 50 ppm. Other loci, such as construction products, oilfield fluids or emulsions, require 0.5 to 5000 ppm of the 3-isothiazolone microbicides to inhibit microorganism growth, while loci such as disinfectants or sanitizers may require up to 5,000 ppm.

It is known in the art that the performance of antimicrobial agents may be enhanced by combination with one or more other antimicrobial agents. Thus, other known microbicidal agents may be combined advantageously with the compositions of the present invention.

The following examples are presented to illustrate further various aspects of the present invention, but are not intended to limit the scope of the invention in any aspect. In the following examples, samples were considered stable when at least 85 percent of the 3-isothiazolones remained after 5 weeks of storage at 55° C.

EXAMPLE 1

Samples of nitrate stabilized 3-isothiazolone concentrate compositions were evaluated for precipitate formation. Eight samples were prepared by weighing into each of eight bottles an amount of a commercial 3-isothiazolone product. To samples A to D was added potassium iodate or sodium iodate. To samples C-1 to C-3 was added copper nitrate, as copper nitrate hemipentahydrate. The ingredients of each sample, reported in wt %, are shown in Table 1. The control sample was just the commercial isothiazolone product containing magnesium nitrate. Samples C-1 to C-3 were comparative. Each sample was then stirred until all salts had dissolved. All samples were clear initially, with no precipitate being present. The samples were stored in an oven at 55° C.

TABLE 1

| | Formulation | | | | | | | |
|---|---|---|---|---|---|---|---|---|
| Ingredients | A | B | C | D | C-1** | C-2** | C-3** | Control |
| 3-Isothiazolones* | 99 | 98 | 99 | 84 | 97.4 | 98.6 | 83.4 | 100 |
| Potassium Iodate | 1 | 2 | | 2 | | | | |
| Sodium Iodate | | | 1 | | | | | |
| Copper Nitrate | | | | | 2.6 | 1.4 | 2.6 | |
| Additional Water | | | | 14 | | | 14 | |
| Total | 100 | 100 | 100 | 100 | 100 | 100 | 100 | 100 |

*14 wt % of a 3:1 mixture of 5-chloro-2-methyl-3-isothiazolone:2-methyl-3-isothiazolone and 16 wt % magnesium nitrate in water.
**Comparative After several weeks storage, the samples were visually inspected for the presence of a precipitate. The control, containing only nitrate as a stabilizer, contained precipitate after storage. Those samples containing copper in addition to nitrate as a stabilizer, that is comparative samples C-1 to C-3, also contained precipitate. Those samples containing the combination of nitrate and iodate as a stabilizer, that is samples A to D, were all free of precipitate. These data show that the combination of metal nitrate and iodate in 3-isothiazolone prevents precipitate formation in 3-isothiazolone concentrate compositions.

EXAMPLE 2

Four concentrate samples were prepared by dissolving 1 through 4 wt % potassium iodate in the commercial 3-isothiazolone concentrate composition used in Example 1. A commercial 3-isothiazolone concentrate composition was used as the control. The samples were prepared as follows. All amounts are in wt %.

| | Formulation | | | | |
|---|---|---|---|---|---|
| Ingredient | Control | E | F | G | H |
| 3-Isothiazolones* | 100 | 99 | 98 | 97 | 96 |
| Potassium Iodate | | 1 | 2 | 3 | 4 |

*14 wt % of a 3:1 mixture of 5-chloro-2-methyl-3-isothiazolone:2-methyl-3-isothiazolone and 16 wt % magnesium nitrate in water.

Once prepared, the samples were divided in half. One half of each sample was stored in an oven at 55° C., the other half of each sample was used in Example 3. The samples were removed from the oven at weekly intervals, aliquots were taken, and the aliquots analyzed by HPLC for the percentage of 3-isothiazolones remaining in each sample. The results are reported in Table 2.

TABLE 2

| Sample | Wt % KIO$_3$ | 1 Week | 2 Weeks | 3 Weeks | 4 Weeks |
|---|---|---|---|---|---|
| Control | 0 | 98.2 | 96.4 | 94.4 | 93.1 |
| E | 1 | 98.5 | 99.0 | 98.2 | 97.1 |
| F | 2 | 99.1 | 98.2 | 95.7 | 97.0 |
| G | 3 | 99.6 | 93.9 | 97.6 | 98.2 |
| H | 4 | 99.4 | 98.8 | 98.9 | 97.4 |

The data clearly show that all samples were stable after 4 weeks storage at 55° C. The samples containing nitrate and iodate as stabilizers were more stable than the control, which contained only nitrate as stabilizer. The samples were also visually inspected at each time point for the formation of precipitate. Visual inspection showed that only the control sample contained precipitate. The use of the combination of nitrate and iodate as a stabilizer for the commercial 3-isothiazolone concentrate samples prevented formation of precipitate.

EXAMPLE 3

A portion of the concentrate samples from Example 2 was diluted with water to form dilute solutions immediately after preparing the concentrate samples. These samples were the time zero weeks storage before dilution samples. At each weekly time point after storage at 55° C. in Example 2, a portion of the stored concentrate samples was removed and diluted with water to form the dilute solution samples used in this example. These samples were 1 to 4 weeks storage at 55° C. before dilution samples. The dilutions were made by making a 10.7 wt % solution of the samples of Example 2 in deionized water. For example 5.35 g of sample 9 were added to 44.65 g of deionized water. The resulting dilute solutions contained 1.5 wt % of 3-isothiazolones. The dilute solution samples were then stored at 55° C. for 12 weeks each and analyzed for 3-isothiazolones remaining. These data are reported in Table 3.

TABLE 3

| Sample | Weeks Storage Before Dilution | Wt % KIO$_3$ | % 3-Isothiazolones Remaining |
|---|---|---|---|
| Control | 0 | 0 | 14 |
| E | 0 | 1 | 96 |
| F | 0 | 2 | 96 |
| G | 0 | 3 | 97 |
| H | 0 | 4 | 96 |
| Control | 1 | 0 | 17 |
| E | 1 | 1 | 97 |
| F | 1 | 2 | 96 |
| G | 1 | 3 | 97 |
| H | 1 | 4 | 95 |
| Control | 2 | 0 | 14 |
| E | 2 | 1 | 100 |
| F | 2 | 2 | 100 |
| G | 2 | 3 | 100 |
| H | 2 | 4 | 100 |
| Control | 3 | 0 | 13 |
| E | 3 | 1 | 85 |
| F | 3 | 2 | 94 |
| G | 3 | 3 | 94 |
| H | 3 | 4 | 95 |

TABLE 3-continued

| Sample | Weeks Storage Before Dilution | Wt % KIO$_3$ | % 3-Isothiazolones Remaining |
|---|---|---|---|
| Control | 4 | 0 | 12 |
| E | 4 | 1 | 80 |
| F | 4 | 2 | 94 |
| G | 4 | 3 | 93 |
| H | 4 | 4 | 92 |

The control sample was not stable after storage as a dilute solution, whereas samples E–H were completely stable after storage as dilute solutions. These data clearly show that 3-isothiazolone concentrates containing metal nitrate and iodate can be diluted before or after storage at 55° C. to form stable dilute solutions without the need for additional stabilizer.

EXAMPLE 4

Five 3-isothiazolone dilute solutions were prepared by diluting a commercially available 3-isothiazolone containing 14 wt % of an approximate 3:1 mixture of 5-chloro-2-methyl-3-isothiazolone ("CMI") and 2-methyl-3-isothiazolone ("MI") and 16 wt % magnesium nitrate in water. For example, the control was prepared by weighing 10.7 g of the commercial 3-isothiazolone concentrate into a bottle and adding 88.8 g of deionized water. The dilute solutions all contained 1.50 wt % 3-isothiazolones. The control contained no additional stabilizer. To samples J, K, and L were added 0.1, 0.5, and 1.0 wt % potassium iodate, respectively. To the fifth sample was added 0.15 wt % copper nitrate, which served as a comparative. The samples were stored in an oven at 55° C. and analyzed for the total wt % of 3-isothiazolone present after 22 weeks. The results are reported in Table 4.

TABLE 4

| Sample | Additional Stabilizer | Wt % 3-Isothiazolones Remaining After Storage |
|---|---|---|
| Control | None | 0.26 |
| J | 0.1 wt % KIO$_3$ | 1.48 |
| K | 0.5 wt % KIO$_3$ | 1.47 |
| L | 1.0 wt % KIO$_3$ | 1.47 |
| Comparative | 0.15 wt % CuNO$_3$ | 1.38 |

These data clearly show that the combination of metal nitrate and iodate was sufficient to stabilize the 3-isothiazolone dilute solution for an extended period of storage. The nitrate and iodate stabilized dilute solution samples showed better stability than the copper stabilized comparative sample.

EXAMPLE 5

Twelve 3-isothiazolone concentrate samples were prepared according to Table 5. The 3-isothiazolones used were an approximate 3:1 mixture of 5-chloro-2-methyl-3-isothiazolone ("CMI") and 2-methyl-3-isothiazolone ("MI"). The samples were prepared by combining the 3-isothiazolone and water followed by the addition of any stabilizer. The amounts of each component in Table 5 are reported in wt %. The magnesium nitrate was added as the hexahydrate. The amount of magnesium nitrate reported is the actual amount of magnesium nitrate present in the compositions. The samples were stored in an oven at 55° C.

and analyzed for the percentage of CMI remaining after 6 weeks storage. The results are reported in Table 5.

TABLE 5

| Sample | CMI + MI | Water | Magnesium Nitrate | Sodium Nitrate | Potassium Iodate | % CMI Remaining |
|---|---|---|---|---|---|---|
| Control | 15 | 70.0 | 15.0 | — | — | 67.1 |
| Comparative | 15 | 80.0 | 5.0 | — | — | 0 |
| M | 15 | 79.0 | 5.0 | — | 1.0 | 97.9 |
| N | 15 | 75.0 | 5.0 | — | 5.0 | 93.8 |
| Comparative | 15 | 70.0 | — | 15.0 | — | 0 |
| Comparative | 15 | 80.0 | — | 5.0 | — | 0 |
| O | 15 | 79.0 | — | 5.0 | 1.0 | 98.7 |
| P | 15 | 75.0 | — | 5.0 | 5.0 | 88.1 |
| Comparative | 25 | 70.0 | 5.0 | — | — | 0 |
| Comparative | 25 | 70.0 | — | 5.0 | — | 0 |
| Q | 25 | 65.0 | 5.0 | — | 5.0 | 88.7 |
| R | 25 | 65.0 | — | 5.0 | 5.0 | 89.7 |

The above data clearly show that the combination of metal nitrate and iodate provides greater stability of 3-isothiazolone concentrates than metal nitrate alone.

EXAMPLE 6

Three samples of isothiazolone concentrates were prepared by combining 11 wt % CMI, 3 wt % MI, 25 wt % sodium nitrate, water, and additional stabilizer. To samples S and T were added 0.20 wt % iodic acid as additional stabilizer. To sample U was added 0.25 wt % potassium iodate as additional stabilizer. The samples were stored in an oven at 55° C. and analyzed for the percent of CMI remaining after 2 weeks storage. The results are reported in Table 6.

| Sample | Additional Stabilizer | % CMI Remaining | % MI Remaining |
|---|---|---|---|
| S | 0.20 wt % HIO₃ | 100 | 100 |
| T | 0.20 wt % HIO₃ | 100 | 100 |
| U | 0.25 wt % KIO₃ | 100 | 100 |

The above data clearly show that a combination of sodium nitrate with a small percentage of iodic acid or iodate was sufficient to stabilize the 3-isothiazolone concentrates for an extended period of storage.

EXAMPLE 7 (COMPARATIVE)

Samples of concentrates and dilute solutions were prepared using the 3-isothiazolones of Example 4. In each case, no metal nitrate was added. The only stabilizer present was potassium iodate. The components of each sample are reported in Table 7. All amounts are wt %. The samples were stored in an oven at 55° C. and analyzed for the percent of CMI remaining after 5 weeks storage. The results are reported in Table 7.

TABLE 7

| Sample | CMI + MI | Water | Potassium Iodate | % CMI Remaining |
|---|---|---|---|---|
| C-4 | 1.5 | 97.5 | 1.0 | 99.1 |
| C-5 | 1.5 | 96.5 | 2.0 | 100 |
| C-6 | 5.0 | 93.0 | 2.0 | 81.7 |
| C-7 | 5.0 | 91.0 | 4.0 | 86.2 |

TABLE 7-continued

| Sample | CMI + MI | Water | Potassium Iodate | % CMI Remaining |
|---|---|---|---|---|
| C-8 | 10.0 | 88.0 | 2.0 | 0 |
| C-9 | 10.0 | 86.0 | 4.0 | 77.3 |
| C-10 | 15.0 | 83.0 | 2.0 | 0 |
| C-11 | 15.0 | 81.0 | 4.0 | 0 |
| C-12 | 20.0 | 78.0 | 2.0 | 0 |
| C-13 | 20.0 | 76.0 | 4.0 | 0 |

The above data show that potassium iodate by itself provides limited to no stability of 3-isothiazolone concentrates.

EXAMPLE 8 (COMPARATIVE)

This example demonstrates that combinations of nitrate with oxidants other than iodic acid, periodic acid, or their salts do not stabilize 3-isothiazolone concentrates. A comparative sample was prepared according to Example 5, except that hydrogen peroxide was added as a stabilizer, in an amount according to Table 8. This comparative sample was compared to Sample O from Example 5. The amounts in Table 8 are reported in wt %, based on the weight of the composition. The samples were stored in an oven at 55° C. and analyzed for the percentage CMI remaining after 6 weeks of storage. The results are reported in Table 8.

TABLE 8

| Sample | CMI + MI | Water | Sodium Nitrate | Iodate | Hydrogen Peroxide | % CMI Remaining |
|---|---|---|---|---|---|---|
| Comparative | 15 | 77.0 | 5.0 | — | 3.0 | 0 |
| O | 15 | 79.0 | 5.0 | 1.0 | — | 98.7 |

From the above data, it can be seen that hydrogen peroxide and metal nitrate do not stabilize 3-isothiazolone concentrates against degradation. However, the combination of a small amount of metal nitrate with iodate stabilizes the 3-isothiazolone concentrate.

What is claimed is:

1. A stable microbicide composition comprising:
   (a) 0.5 to 35 wt %, based on the weight of the composition, of a water soluble 3-isothiazolone;
   (b) 0.2 to 30 wt %, based on the weight of the composition, of a metal nitrate selected from the group consisting of lithium nitrate; sodium nitrate; potassium nitrate; magnesium nitrate; calcium nitrate; and ammonium nitrate;

(c) 0.01 to 35 wt %, based on the weight of the composition, of iodic acid, periodic acid, or their salts; and (d) water;

wherein the weight ratio of (b) to (a) is 25:1 to 1:25, and the composition is precipitate free.

2. The composition of claim 1 wherein the 3-isothiazolone compound is selected from the group consisting of 5-chloro-2-methyl-3-isothiazolone; 2-methyl-3-isothiazolone; 2-ethyl-3-isothiazolone; 5-chloro-2-ethyl-3-isothiazolone; 4,5-dichloro-2-methyl-3-isothiazolone; and mixtures thereof.

3. The composition of claim 1 wherein the iodic acid salt or periodic acid salt is selected from the group consisting of lithium iodate; sodium iodate; potassium iodate; ammonium iodate; lithium periodate; sodium periodate; potassium periodate; and ammonium periodate.

4. The composition of claim 1 wherein the 3-isothiazolone compound is present in an amount of 5 to 35 wt %, based on the weight of the composition.

5. The composition of claim 1 wherein the 3-isothiazolone is present in an amount of 5 to 25 wt %, based on the weight of the composition, the metal nitrate is present in an amount of 1 to 25 wt %, based on the weight of the composition, and the iodic acid, periodic acid, or their salts is present in an amount of 0.05 to 10 wt %, based on the weight of the composition.

6. The composition of claim 5 wherein the iodic acid, periodic acid, or their salts is selected from the group consisting of iodic acid, sodium iodate, potassium iodate, and sodium periodate.

7. A method of preventing precipitate formation in a microbicide composition comprising the step of adding 0.2 to 30 wt %, based on the weight of the composition, of a metal nitrate selected from the group consisting of lithium nitrate; sodium nitrate; potassium nitrate; magnesium nitrate; calcium nitrate; and ammonium nitrate to a stabilized 3-isothiazolone composition comprising 0.5 to 35 wt %, based on the weight of the composition, of a water soluble 3-isothiazolone compound; 0.01 to 35 wt %, based on the weight of the composition, of iodic acid, periodic acid, or their salts; and water; wherein the weight ratio of metal nitrate to 3-isothiazolone compound is 25:1 to 1:25.

8. The method of claim 7 wherein the 3-isothiazolone compound is selected from the group consisting of: 5-chloro-2-methyl-3-isothiazolone; 2-methyl-3-isothiazolone; 2-ethyl-3-isothiazolone; 5-chloro-2-ethyl-3-isothiazolone; 4,5-dichloro-2-methyl-3-isothiazolone; and mixtures thereof.

9. The method of claim 7 wherein the iodic acid salt or periodic acid salt is selected from the group consisting of: lithium iodate; sodium iodate; potassium iodate; ammonium iodate; lithium periodate; sodium periodate; potassium periodate; and ammonium periodate.

10. A method of controlling or inhibiting the growth of microorganisms in a locus comprising introducing to the locus the composition of claim 1.

11. The method of claim 10 wherein the locus is selected from the group consisting of: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings; and metal working fluids.

* * * * *